US011826309B2

(12) United States Patent
Gallegos

(10) Patent No.: US 11,826,309 B2
(45) Date of Patent: Nov. 28, 2023

(54) THERAPY DEVICE

(71) Applicant: Lenore C. Gallegos, Denver, CO (US)

(72) Inventor: Lenore C. Gallegos, Denver, CO (US)

( * ) Notice: Subject to any disclaimer, the term of this patent is extended or adjusted under 35 U.S.C. 154(b) by 521 days.

(21) Appl. No.: 17/020,163

(22) Filed: Sep. 14, 2020

(65) Prior Publication Data
US 2022/0079846 A1 Mar. 17, 2022

(51) Int. Cl.
A61J 17/02 (2006.01)
A61J 17/00 (2006.01)

(52) U.S. Cl.
CPC ............ A61J 17/02 (2013.01); A61J 17/113 (2020.05); A61J 2200/50 (2013.01)

(58) Field of Classification Search
CPC .......... A61J 17/00; A61J 17/001; A61J 17/02; A61J 17/10; A61J 17/107; A61J 2200/50; A61J 2200/44; A61J 2200/42; A61H 2201/02; A61H 2201/0207; A61H 2201/0214; A61H 2201/0221; A61H 2201/0242; A47G 19/2205; A47G 19/2288; A61F 7/00; A61F 2007/0001; A61F 2007/0054; A61F 2007/0059; A61F 2007/0056; A61F 7/086; A61F 7/10; A61F 7/103; A61F 2007/105; A61F 2007/108; A61F 7/02; A61F 2007/0203; A61F 2007/0215; A61F 2007/0217; A61F 2007/0219; A61F 2007/0222; A61F 2007/0223; A61F 2007/0277

See application file for complete search history.

(56) References Cited

U.S. PATENT DOCUMENTS

| 3,669,117 | A | * | 6/1972 | Herbst | A61J 17/001 |
| | | | | | 606/235 |
| 8,182,510 | B2 | | 5/2012 | Brabant et al. | |
| 8,361,115 | B2 | | 1/2013 | Brabant et al. | |
| 2009/0299410 | A1 | * | 12/2009 | Brabant | A61J 17/02 |
| | | | | | 606/235 |
| 2020/0022882 | A1 | | 1/2020 | Aslan et al. | |
| 2020/0237126 | A1 | * | 7/2020 | Booska | A47G 19/2266 |

FOREIGN PATENT DOCUMENTS

| CN | 2762682 | Y | * | 3/2006 | |
| CN | 107744313 | A | * | 3/2018 | |
| CN | 108814194 | A | * | 11/2018 | |
| EP | 3381333 | A1 | * | 10/2018 | ......... A47G 19/2272 |

* cited by examiner

Primary Examiner — Katherine M Shi

(57) ABSTRACT

A cold and/or hot therapy device that utilizes insulation to maintain its temperature.

16 Claims, 6 Drawing Sheets

THERAPY DEVICE

BACKGROUND

Cold therapy and heat therapy have been a recommended treatment for pain for decades. Commonly, this therapy was provided via an ice bag or heating pad which was held against the injured or painful area. More recently, improved devices have been developed for use in providing cold and hot therapy.

Reusable hot and/or cold packs generally contain a viscous solution, suspension, or gel, mostly aqueous or glycol-based, that is cooled or frozen in a refrigerator or freezer and/or heated in a microwave. These device may retain temperatures longer than ice or water alone. However, these viscous solutions are often poisonous or harmful if ingested. As such, there is a need for a therapy device that maintains its temperature without the use of substances that are harmful if ingested.

SUMMARY

The techniques of this disclosure generally relate to a therapy device that can maintain its temperature while not having to utilize any substances that are harmful for human consumption.

In one aspect, the present disclosure provides a cold therapy device. The cold therapy device includes a stainless steel exterior body, a stainless steel interior reservoir, and a chamber located between the exterior body and the interior reservoir. The chamber is sealed. Insulation is located in the chamber. A first opening provides access to the interior reservoir at first end but no access to the chamber. A second opening provides access to the interior reservoir at a second end but no access to the chamber. A first lid is provided that creates a liquid and airtight seal for the first opening in a sealed position. A second lid is provided that creates a liquid and airtight seal for the second opening in a sealed position.

In another aspect, the disclosure provides a therapy device. The therapy device includes a stainless steel exterior body, a stainless steel interior reservoir, and a chamber located between the exterior body and the interior reservoir. The chamber is sealed and has insulation located inside of it. An opening provides access to the interior reservoir but not to the chamber. A lid creates a liquid and airtight seal for the opening in a sealed position.

In another aspect, the disclosure provides a therapy device. The therapy device includes a first stainless steel exterior body, a first stainless steel interior reservoir and a first chamber located between the first exterior body and the first interior reservoir. The first chamber is sealed and has insulation location inside it. A first opening provides access to the first interior reservoir but no access to the first chamber. The therapy device also includes a second stainless steel exterior body, a second stainless steel interior reservoir, and a second chamber located between the second exterior body and the second interior reservoir. The second chamber is sealed and has insulation located inside of it. A second opening provides access to the second interior reservoir but no access to the second chamber. The therapy device also includes a connector that connects the first exterior body to the second exterior body.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

As discussed above, previously utilized reusable cold packs generally contain a viscous solution, suspension, or gel, mostly aqueous or glycol-based, that is cooled or frozen in a refrigerator or freezer. These device may retain colder temperatures longer than ice or water alone. However, these viscous solutions are often poisonous or harmful if ingested. As such, there is a need for a therapy device that maintains its temperature without the use of substances that are harmful if ingested.

Figure 1:
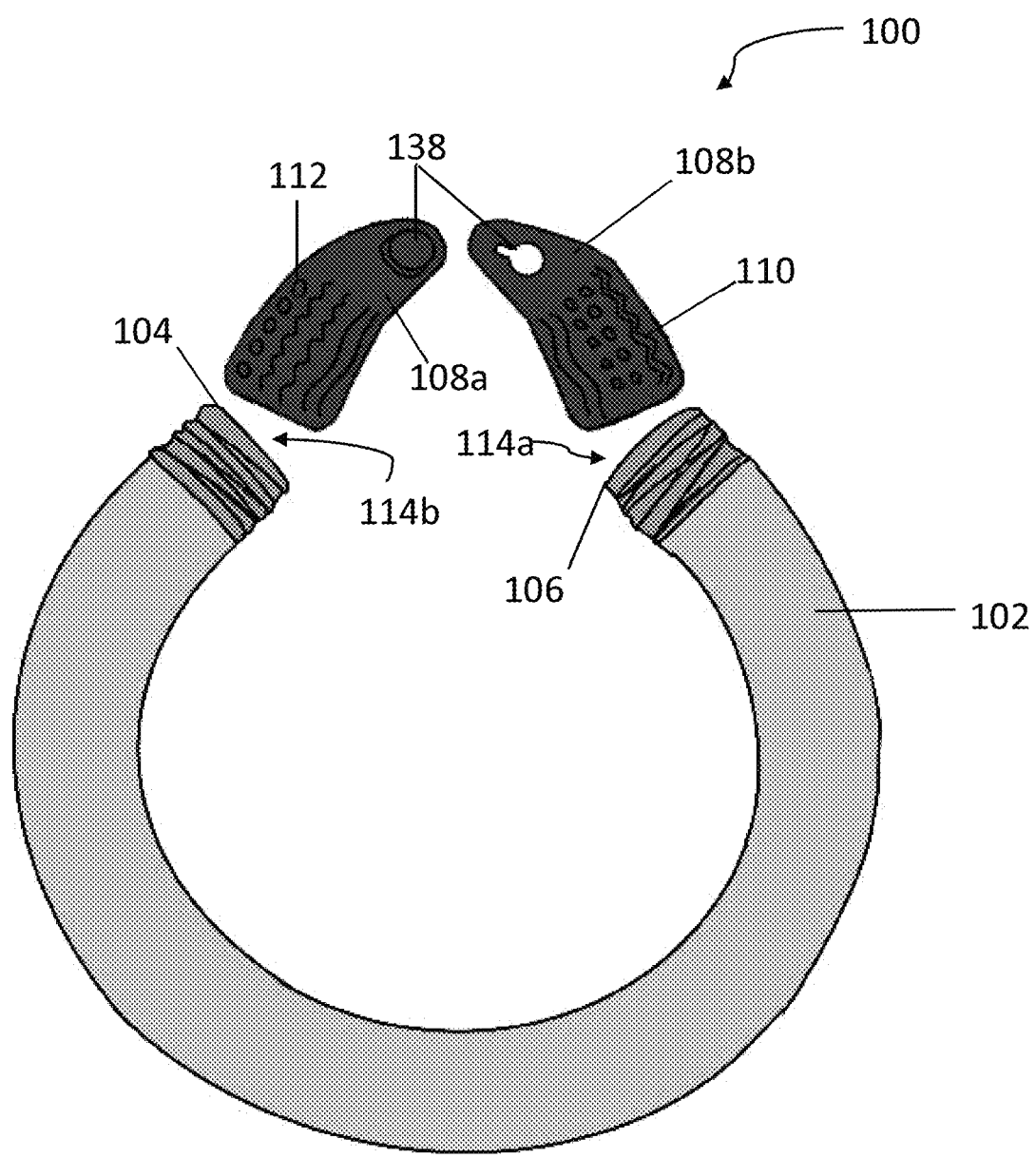
FIG. 1 is a picture that illustrates one configuration of a therapy device.
Figure 2:
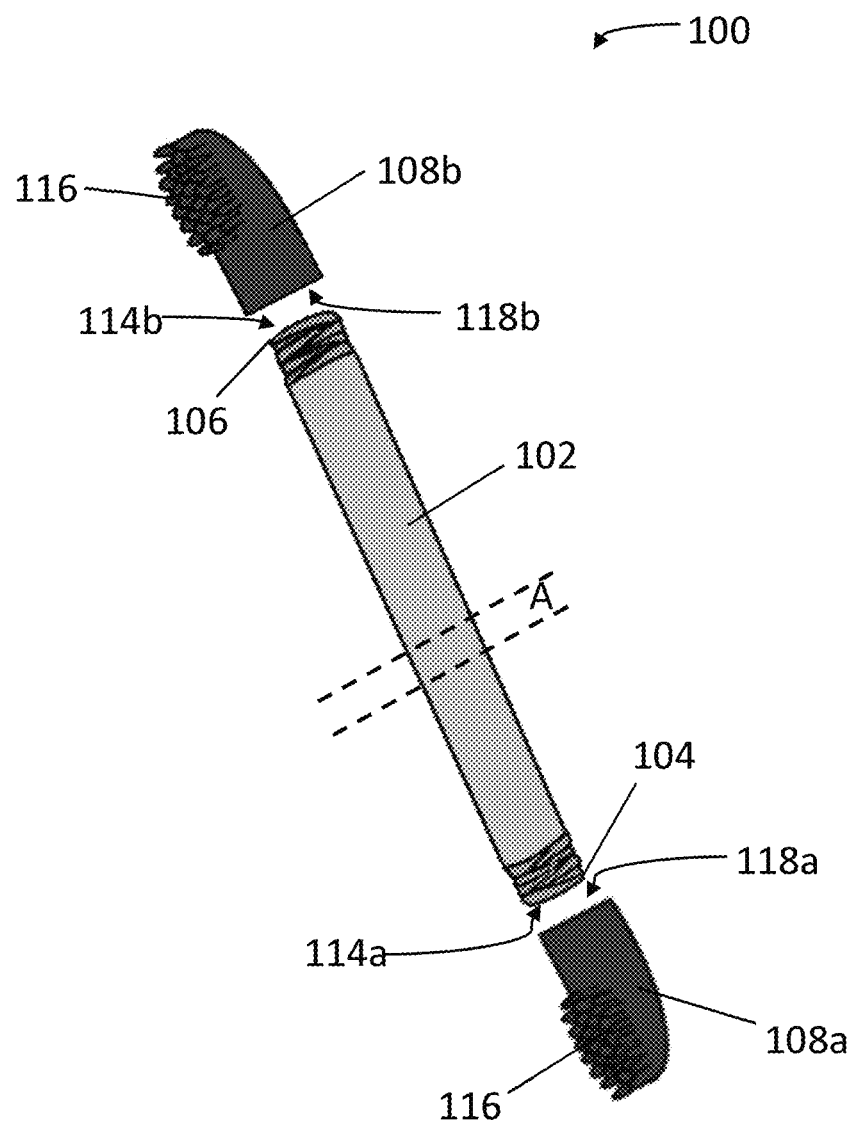
FIG. 2 is a picture that illustrates one configuration of a therapy device.
Figure 3:
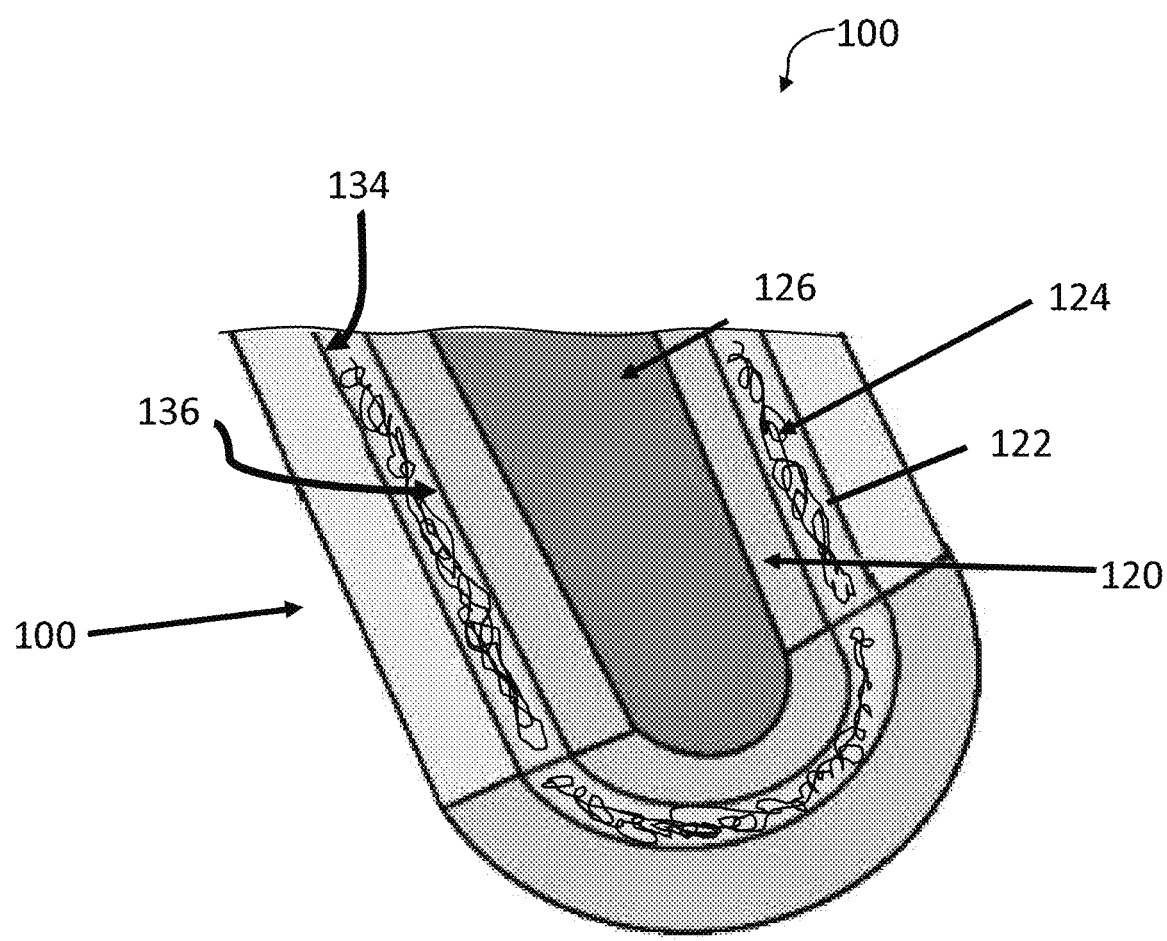
FIG. 3 is a partial, axial, cross-sectional schematic diagram of area A of FIG. 2.
Figure 4:
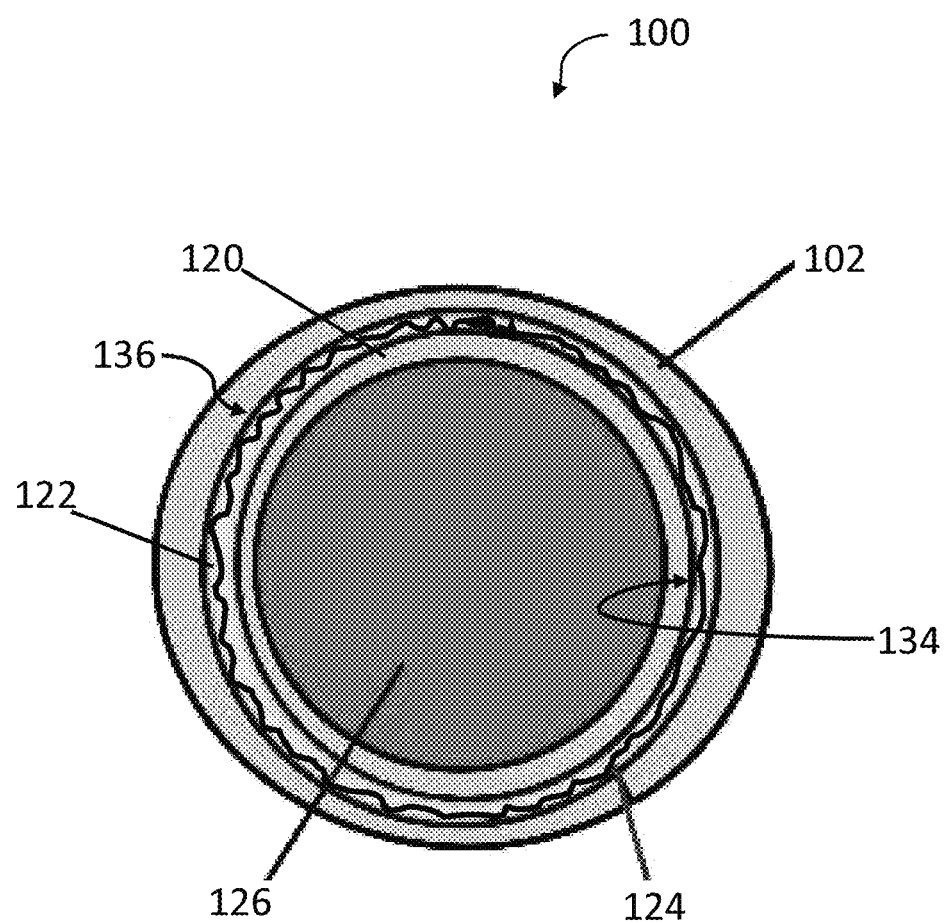
FIG. 4 is a partial, transverse, cross-sectional schematic diagram of area A of FIG. 2.
Figure 5:
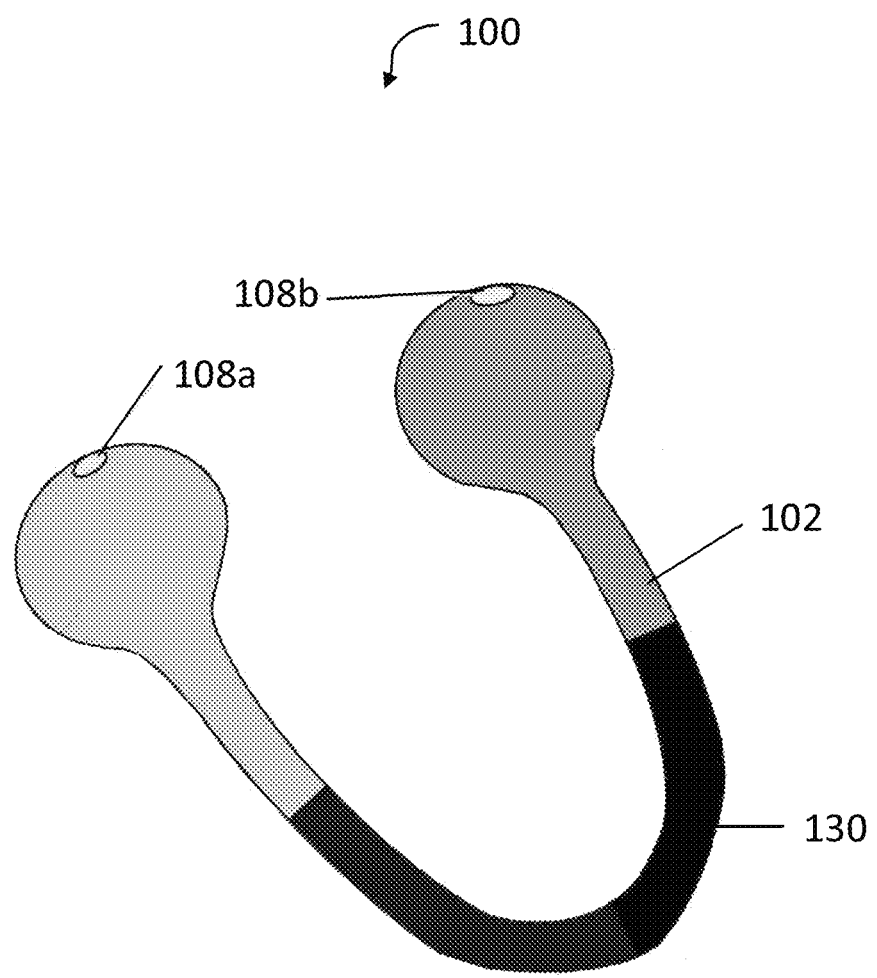
FIG. 5 is a picture that illustrates one configuration of a therapy device.
Figure 6:
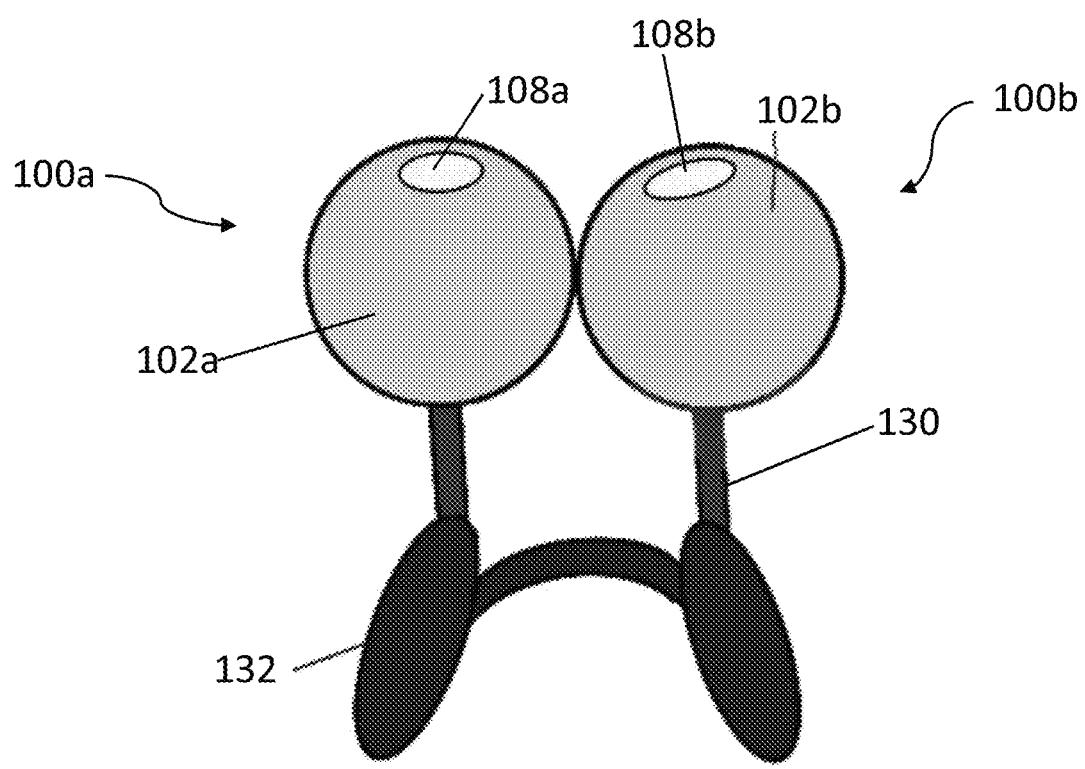
FIG. 6 is a picture that illustrates one configuration of a therapy device.

FIGS. 1, 2, 5 and 6 are pictures that illustrate different configurations of a cold and/or hot therapy device 100. FIG. 3 is a partial, axial, cross-sectional schematic diagram of area A of FIG. 2 and FIG. 4 is a partial, transverse, cross-sectional schematic diagram of area A of FIG. 2. The therapy device 100 includes an exterior body 102, an interior reservoir 120, and a chamber 122. The therapy device 100 may be shaped as desired to provide cold and/or hot therapy. For example, the therapy device 100 may be a cylinder that is in a U-shape or semi-circle shape as illustrated in FIG. 1. In other aspects, the therapy device 100 may be a straight cylinder as illustrated in FIG. 2. In further aspects, the therapy device 100 may be shaped to attach to or conform to the anatomy of person. For example, FIGS. 5 and 6 illustrate a therapy device 100 that is shaped to rest on or attach to the bridge of the nose while providing cold and/or hot therapy to a pressure point located near the area. In another aspect, the therapy device 100 is a teether for babies and/or children as illustrated by FIGS. 1 and 2. The shapes provided for the therapy device 100 herein are exemplary. Any suitable shape for providing cold and/or hot therapy to a patient may be utilized by the therapy device 100 as would be known by a person of skill in the art.

In some aspects, the exterior body 102, the interior reservoir 120, and the chamber 122 are made of metal. In further, aspects, the exterior body 102, the interior reservoir 120, and the chamber 122 are made of stainless steel or steel. In other aspects, the exterior body 102, the interior reservoir 120, and the chamber 122 are made of different materials, such as metal, plastic, and/or rubber. In some aspects, the exterior body 102, the interior reservoir 120, and/or the chamber 122 are made of silicone. These examples are not meant to be limiting. Other materials may be utilized to make the exterior body 102, the interior reservoir 120, and/or the chamber 122 as would be known by a person of skill in the art.

The chamber 122 is located between the exterior body 102 and the interior reservoir 120. The chamber 122 has an inner side 134 and an outer side 136. The chamber 122 is sealed. As such, the chamber 122 does not allow water in or out of the chamber 122. In some aspects, the chamber 122 does not allow air in or out of the chamber 122. The chamber 122 may be filled with insulation 124. The insulation 124 may be any natural fiber insulation. Examples of natural fiber insulation includes wool and cotton. These examples are not meant to be limiting. Other natural fiber insulation may be utilized as would be known by a person of skill in the art.

The therapy device 100 includes at least one opening 114. The opening 114 provides access to the interior reservoir 120 but not to the chamber 122. The opening 114 extends past the exterior body 102 and chamber 122 to provide access to the interior reservoir 120. In some aspects, the interior reservoir 120 is located entirely within the chamber 122 except for at the opening 114. In other aspects, at least a portion of the interior reservoir 120 is located adjacent to an outer side 136 of the chamber 122. In these aspects, the location of the liquid contact with the outer side 136 and exterior body 102 may be specifically positioned to provide hot and/or cold liquid contact to a specific exterior portion of the therapy device 100 and/or positioned to provide hot and/or cold therapy to a specific anatomy of the user or patient. The opening 114 allows a user of the therapy device 100 to add liquid 126 to the interior reservoir. The liquid 126 may be any temperature as desired for treatment, such as cold, hot, warm, or cool. In some aspects, the liquid 126 is water. In further aspects, ice may be added via the opening 114 with or without the liquid 126 to the internal reservoir 120. In further aspects, the therapy device 100 includes multiple openings 114 that provide access to the internal reservoir 120.

The therapy device 100 includes at least one lid 108. In some aspects, the therapy device 100 includes a lid 108 for each opening 114 as illustrated in FIGS. 1, 2, 5 and 6. In other aspects, a single lid 108 covers multiple openings 114. For example, FIGS. 1 and 2 illustrate a first lid 108a that covers a first opening 114a and a second lid 108b that convers a second opening 114b. The lid 108 creates a liquid and/or airtight seal for the opening 114 in a sealed position. The lid 108 may connect to the cold therapy device 100 utilizing any suitable connection, such as twist on, snap fit, clip configuration, etc. For example, FIGS. 1 and 2 illustrate a twist on connector with threads. The lid 108 in the open position provides the user of the therapy device 100 access to the opening 114. In some aspects, the lid 108 in the open position is removable and separable from the exterior body 102. In other aspects, the lid 108 in the open position provides access to the internal reservoir 120, but remains connected or coupled to the exterior body 102 of the therapy device 100. The lid 108 may be made of any desirable material, such as metal, plastic, or rubber. In some aspects, the lid 108 is made of silicone. In other aspects, the lid 108 is made of stainless steel. These example lid 108 materials are not meant to be limiting. Other materials may be utilized to make the lid 108 as would be known by a person of skill in the art. In additional aspects, the at least one lid 108 includes a texture or is textured. The texture may be bumps 112, rivets, patterned, bristles 116 or etc. For example, FIG. 1 shows bumps 112 and raised line textures 110. In another example, FIG. 2 shows bristles 116 as a texture. These textures are exemplary only. Any suitable texture 128 for the lid of a cold therapy device 100 may be utilized as would be know by a person of skill in the art.

In some aspects, the lid 108 includes a lid reservoir 118 that connects to the interior reservoir 120 when the lid 108 is in the sealed position. In this aspect, the liquid 126 from the interior reservoir 120 can flow from the interior reservoir 120 via the opening 114 into the lid reservoir 118 when in the sealed position. In other aspects, if the lid 108 connects to multiple openings 114, the lid reservoir 118 may connect via multiple different openings 114 to the interior reservoir 120. In this aspect, liquid 126 can flow via the different openings 114 from the interior reservoir 120 to the lid reservoir 118, when the lid 108 is in the sealed position. In other aspects, each lid 108 or only a portion of the lids 108 utilized may include a lid reservoir 118. In another example, FIG. 2 illustrates a first lid 108a with a first lid reservoir 118a that covers a first opening 114a at a first end 104 and a second lid 108b with a second lid reservoir 118b that convers a second opening 114b at a second end 106. In some aspect, the cold or hot temperature of the liquid 126 inside the therapy device 100 is only provided to the user or patient through the lid 108. In other aspects, the cold or hot temperature of the liquid 126 inside the therapy device 100 is provided to the user or patient through the lid 108 and other portions of the therapy device 100. In other aspect, the cold or hot temperature of the liquid 126 inside the therapy device 100 is not provided to the user or patient through the lid 108.

In further aspects, separate lids 108 may be coupled to each other via a coupling device 138. For example, FIG. 1 shows a button slide coupling device 138 for attaching a first lid 108a with a second lid 108b. The coupling device 138 may be any suitable mechanism for coupling one or more lids 108 together while in the sealed position and/or open position, such as a button, snap, hook and loop, and/or other type of coupling device.

In other aspect, a portion of the therapy device 100 may be covered with a liner 130. In some aspects, the liner 130 minimizes or prevents the transmission of hot and cold temperatures of the cold therapy device 100 to the user. The liner 130 may also be utilized to soften portions of the contact areas of the therapy device 100 to make the therapy device more comfortable for the user. For example, FIG. 5 shows a cold therapy device 100 with a liner 130 for protecting the bridge of the nose from the hot and cold temperature of the therapy device 100 and softens the contact with the bridge of the nose. The liner 130 may be made of any suitable material or combination of materials, such as cotton, polyester, wool, latex, rubber, and etc.

In further aspect, multiple therapy devices 100 may be coupled together via connector 132. The connector 132 may be made of any suitable material for connecting the two separate cold therapy device 100, such as plastic, rubber, metal, etc. The connector 132 may be any suitable shape for connecting multiple therapy device 100 together. For example, FIG. 6 illustrates a connector 132 that is shaped to conform around the bridge of the nose that connects a first therapy device 100a that includes a first exterior body 102a, a first chamber and a first interior reservoir that is sealed with a first lid 108a to a second therapy device 100b that includes a second exterior body 102b, a second chamber, and a second interior reservoir that is sealed with a second lid 108b. The connector may even include hinges, bendable portions, pivotable portions, or etc. for conforming to body shapes to allow the therapy devices 100 to contact the desired sections of the user's body more effectively. In other aspect, the liner 130 may be utilized to soften the connector 132.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A cold therapy device, comprising:
   a stainless steel exterior body;
   a stainless steel interior reservoir;
   a chamber located between the exterior body and the interior reservoir, wherein the chamber is sealed;
   insulation located in the chamber;
   a first opening that provides access to the interior reservoir at first end but no access to the chamber;
   a second opening that provides access to the interior reservoir at a second end but no access to the chamber;
   a first lid that creates a liquid and airtight seal for the first opening in a sealed position; and
   a second lid that creates a liquid and airtight seal for the second opening in a sealed position.

2. The cold therapy device of claim 1, wherein the first lid and the second lid are made of silicone.

3. The cold therapy device of claim 2, wherein the first lid includes a first lid reservoir that connects to the interior reservoir via the first opening in the sealed position and the second lid includes a second lid reservoir that connects to the interior reservoir via the second opening in a sealed position.

4. The cold therapy device of claim 3, wherein the first lid and the second lid are textured.

5. The cold therapy device of claim 3, where the cold therapy device is a teether.

6. The cold therapy device of claim 1, wherein the interior reservoir is located entirely within the chamber except for at the first opening and the second opening.

7. The cold therapy device of claim 1, wherein at least a portion of the interior reservoir is located adjacent to an outer side of the chamber.

8. The cold therapy device of claim 1, wherein the insulation is a natural fiber.

9. A therapy device, comprising:
   a stainless steel exterior body;
   a stainless steel interior reservoir;
   a chamber located between the exterior body and the interior reservoir, wherein the chamber is sealed;
   insulation located in the chamber;
   an opening that provides access to the interior reservoir but not to the chamber; and
   a lid that creates a liquid and airtight seal for the opening in a sealed position,
   wherein the lid includes a lid reservoir, wherein the lid reservoir connects to the interior reservoir via the opening in the sealed position.

10. The therapy device of claim 9, where the lid is comprised of silicone.

11. The therapy device of claim 10, where the exterior body is U-shaped.

12. The therapy device of claim 9, where the therapy device is a teether.

13. The therapy device of claim 12, wherein the interior reservoir is located entirely within the chamber except for at the opening.

14. The therapy device of claim 9, wherein the insulation is a natural fiber.

15. The therapy device of claim 14, wherein the natural fiber is cotton or wool.

16. A therapy device, comprising:
   a stainless steel exterior body;
   a stainless steel interior reservoir;
   a chamber located between the exterior body and the interior reservoir, wherein the chamber is sealed;
   insulation located in the chamber;
   an opening that provides access to the interior reservoir but not to the chamber; and
   a lid that creates a liquid and airtight seal for the opening in a sealed position,
   where the exterior body is U-shaped.

* * * * *